(12) United States Patent
Musitano et al.

(10) Patent No.: US 11,311,550 B2
(45) Date of Patent: Apr. 26, 2022

(54) TREATMENT FOR CELLULITIS AND PRE-OPERATIVE TREATMENT

(71) Applicants: Multimode Medical Holdings Inc., Mississauga (CA); Paul Zalzal, Oakville (CA)

(72) Inventors: Patrick Musitano, Hamilton (CA); Paul Zalzal, Oakville (CA)

(73) Assignees: Multimode Medical Holdings Inc., Hamilton (CA); Paul Zalzal, Oakville (CA)

( * ) Notice: Subject to any disclaimer, the term of this patent is extended or adjusted under 35 U.S.C. 154(b) by 0 days.

(21) Appl. No.: 16/729,670

(22) Filed: Dec. 30, 2019

(65) Prior Publication Data

US 2020/0206238 A1 Jul. 2, 2020

Related U.S. Application Data

(60) Provisional application No. 62/785,758, filed on Dec. 28, 2018.

(51) Int. Cl.
| | | |
|---|---|---|
| *A61K 31/545* | (2006.01) | |
| *A61K 31/167* | (2006.01) | |
| *A61K 31/192* | (2006.01) | |
| *A61K 9/00* | (2006.01) | |

(52) U.S. Cl.
CPC .......... *A61K 31/545* (2013.01); *A61K 9/0014* (2013.01); *A61K 31/167* (2013.01); *A61K 31/192* (2013.01)

(58) Field of Classification Search
CPC .................................................... A61K 31/567
USPC ........................................................ 514/179
See application file for complete search history.

(56) References Cited

PUBLICATIONS

Dillon, J. Am. Aca. Dermatology (1983), vol. 8(2), pp. 177-181.*
Kosar, CA Family Phys. (2017) vo. 63, pp. 65-618.*
Ramakrishnan et al., Am. Family Phys. (2015) vol. 92(6), pp. 474-483.*

\* cited by examiner

*Primary Examiner* — Taofiq A Solola
(74) *Attorney, Agent, or Firm* — Blue Filament Law PLLC

(57) ABSTRACT

A composition for the treatment of cellulitis is provided that includes an antibiotic. The composition may also include an analgesic, an anaesthetic, or a combination thereof. A method use is also provided by which the composition is applied topically or to affected skin. A method of use is also provided prior to a medical procedure involving an incision through the skin of a patient in a predetermined area, the method including the application, to the predetermined area and prior to the procedure of the composition.

14 Claims, 2 Drawing Sheets

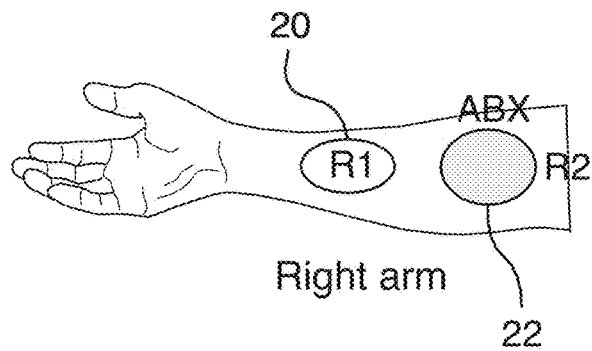
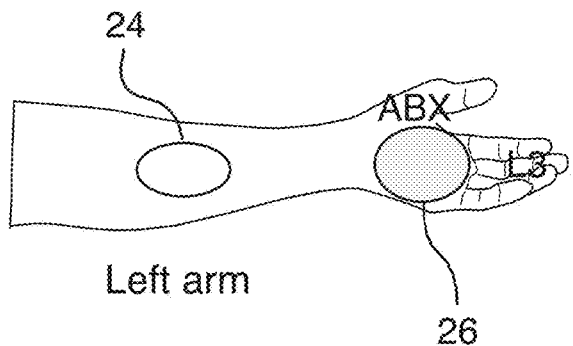
FIG.1　　FIG.2
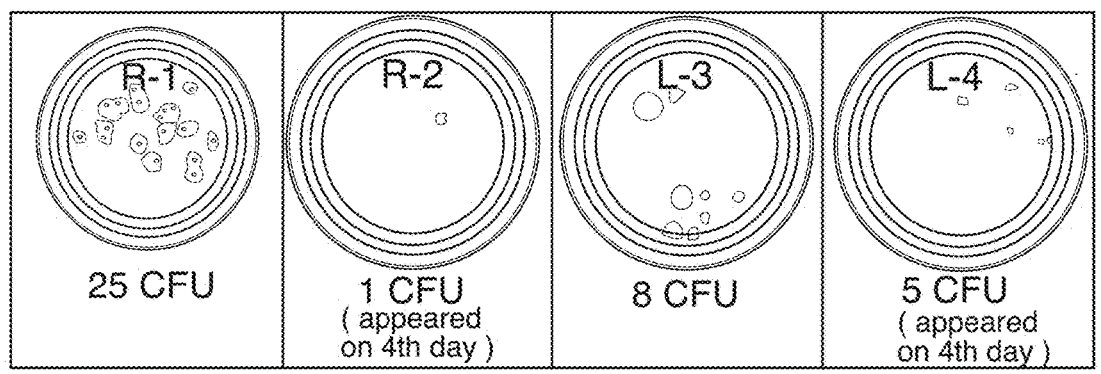
FIG.3　　FIG.4　　FIG.5　　FIG.6

Right arm　　　　　Left arm

TREATMENT FOR CELLULITIS AND PRE-OPERATIVE TREATMENT

CROSS-REFERENCE TO RELATED APPLICATIONS

This application claims priority to U.S. Provisional Patent Application Ser. No. 62/785,758, filed Dec. 28, 2018 and hereby incorporates this provisional application by reference in its entirety.

FIELD OF THE INVENTION

The invention relates to cellulitis.

SUMMARY

Forming one aspect of the invention is a composition for the treatment of cellulitis, the composition comprising an antibiotic.

According to another aspect, the composition can be applied topically.

According to another aspect, in each application, the composition is applied to the infected skin.

According to another aspect, in each application, between about 0.25 gram and about 1 gram of the composition is applied to the skin.

According to another aspect, the density of the composition can be about 1 gram per milliliter.

According to another aspect, the composition can comprise about 5% antibiotic by weight.

According to another aspect, the antibiotic can be Cephalexin.

According to another aspect, the composition can comprise about 5% analgesic by weight.

According to another aspect, the analgesic can be Ketoprofen.

According to another aspect, the composition can comprise about 5% anaesthetic by weight.

According to another aspect, the anaesthetic can be Lidocaine.

According to another aspect, the composition can comprise about 85% transdermal cream by weight.

According to another aspect, the composition can be applied at a rate of about twice daily so long as the cellulitis persists.

Forming another aspect of the invention is a method for use in association with a procedure involving an incision through the skin of a patient in a predetermined area, the method comprising the application, to the predetermined area and prior to the procedure, of the composition.

According to another aspect, the area can be defined by an area which extends about 2 cm beyond the incision.

According to another aspect, the application can be carried out up to about twelve hours preceding the incision.

BRIEF DESCRIPTION OF THE FIGURES

FIG. 1 is a photograph of an arm;
FIG. 2 is a photograph of an arm;
FIG. 3 is a photograph of a RODAC plate;
FIG. 4 is a photograph of a RODAC plate;
FIG. 5 is a photograph of a RODAC plate;
FIG. 6 is a photograph of a RODAC plate.

DETAILED DESCRIPTION OF EMBODIMENTS OF THE INVENTION

Composition

Figures 7, 8:
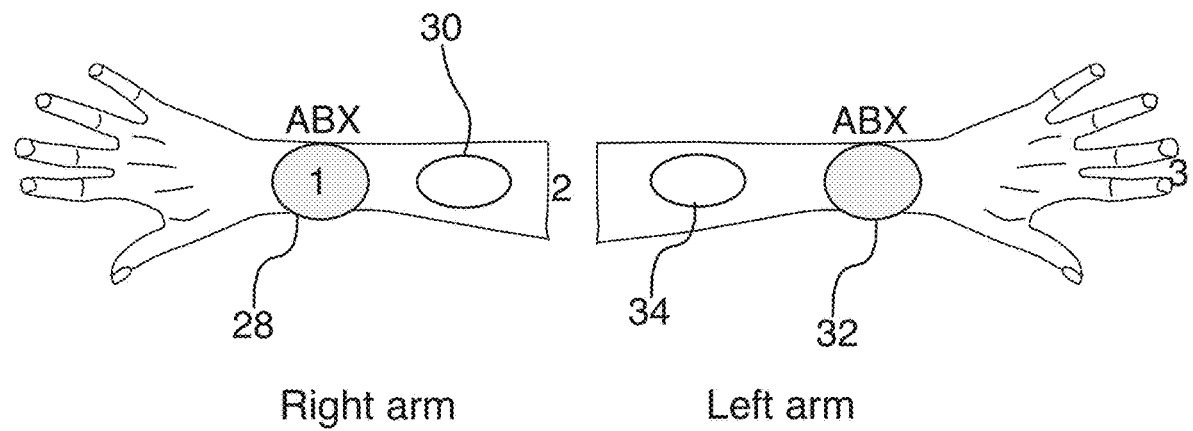
FIG. 7 is a photograph of an arm.
FIG. 8 is a photograph of an arm.
Figures 9, 10, 11, 12:
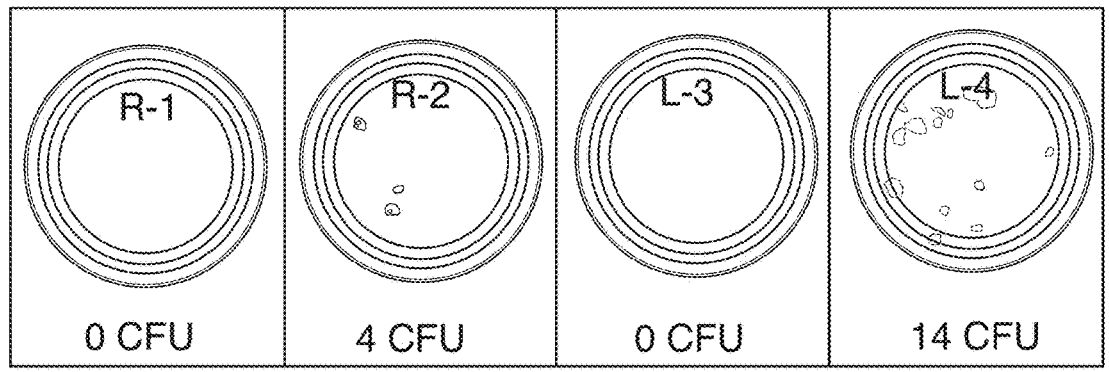
FIG. 9 is a photograph of a RODAC plate.
FIG. 10 is a photograph of a RODAC plate.
FIG. 11 is a photograph of a RODAC plate.
FIG. 12 is a photograph of a RODAC plate.

A composition according to an embodiment of the invention has a density of about 1 gram per milliliter and comprises, by weight: about 85% transdermal cream; about 5% Cephalexin; about 5% Ketoprofen; and about 5% Lidocaine.

The transdermal cream comprises about 15 parts oil phase and about 55 parts poloxamer gel phase.

The oil phase is produced by mixing 50 parts granular soya lecithin, 50 parts isopropyl palmitate (USP-NF), and 1.3 parts sorbic acid (USP-NF) powder; this mixture is allowed to sit until a syrup that looks similar to motor oil is produced, which process takes a few hours.

The poloxamer 20% gel phase is produced by mixing 200 parts poloxamer 407, 3 parts potassium sorbate and 800 parts purified cold water, and allowing the resulting mixture to stand for approximately 24 hours in cold conditions, such as in a refrigerator.

Post-Surgical Embodiment

In an embodiment of the invention, cellulitis is treated through the twice daily application of the composition to the infected skin, the treatment being performed so long as the cellulitis persists, the composition being applied in an amount, per application, of between about 0.25 and about 1 gram, and the treatments being between about 6 and 12 hours apart. If a scheduled dose is delayed, but can be applied such that the next scheduled dose will still fall in the 6-12 hour range, the delayed dose may be so applied; a double quantity should not be applied nor should doses be applied immediately after one another.

Pre-Surgical Embodiment

Another embodiment of the invention is a method for use in association with a procedure involving an incision through the skin of a patient in a predetermined area, the method comprising the application, to an area of the skin which extends about 2 cm beyond the incision and up to about twelve hours prior to the procedure, of the composition in an amount between about 0.5 and about 1 gram.

Post-Surgical Experimental Results

The utility of the post-surgical embodiment will be evident upon review of the following experimental results, each being associated with use of such embodiment described above.

A 74 year old man who presented 2 weeks following an uncomplicated total knee replacement. He had developed swelling blisters around the knee with painful cellulitis around the blisters (soft tissue infection). He was started on oral antibiotics in a conventional amount and the composition. He was re-assessed a mere two weeks later and the cellulitis had surprisingly already been resolved.

A 70 year old woman who presented 11 days after total knee replacement surgery. She had developed redness around the incision and had been started on oral antibiotics 5 days previously. On examination at day 11, she still had redness, warmth and pain indicative of ongoing cellulitis. She was started on the composition. She was re-assessed one week later and her cellulitis had surprisingly already resolved; usually when oral antibiotics fail, IV antibiotics are required.

A 70 year old man presented 10 days post total knee replacement. He had developed painful cellulitis around the incision and was started him on oral antibiotics and the composition. His cellulitis resolved within the next week which was surprising since it typically takes much longer than a week for soft tissue infections such as cellulitis to resolve without IV antibiotics.

An 85 year old woman who had her leg run over by a scooter while on a cruise presented 5 days after the injury. She had a healing abrasion over her ankle with underlying poor blood supply in her leg. Her leg was red and swollen and warm to the touch above the ankle to the knee. She had developed cellulitis from the injury. She was started on oral antibiotics and the composition. One week later her leg was found to be improving. Two further weeks later, her cellulitis had surprising resolved, notwithstanding that in situations such as this, wherein the area of infection was so expansive, IV antibiotics are usually indicated.

A 63 year old woman presented 4 weeks post left total hip replacement with cellulitis in her left foot characterized by pain, redness and swelling. She was started on oral antibiotics and the composition. When she was reassessed two weeks later the cellulitis had resolved with decreased redness, swelling and pain. This was surprisingly fast, given that the artificial joint presents as an excellent host for infection.

A 42 year old woman recovering from an ankle fracture at the talus was being treated in an air cast walking boot. At 3 weeks post injury she developed cellulitis in the same foot and ankle characterized by pain, redness and swelling. She was treated with oral keflex and the composition. She was seen again 1 week later and the cellulitis had resolved. This is much quicker than typical resolution of cellulitis if it was treated with oral antibiotics alone.

A 75 year old man having had a previous right total knee replacement was in a low energy snowmobile accident and developed a seroma on the inner thigh of the same leg. He developed a superficial infection. A trial of oral antibiotics and the composition. His infection turned out to be deep and in the seroma. He required surgical excision of the seroma for cure.

A 68 year old man presented 10 days post total knee replacement with pain, redness, swelling and stiffness in the knee. He was diagnosed with post-operative infection. Instead of the typical treatment involving intravenous antibiotics, a trial of oral antibiotic and the composition was commenced. At 17 days post op he was reassessed and it was surprisingly found that his cellulitis had resolved, he had less redness, swelling and pain and his stiffness was resolving.

A 64 year old man who developed a large area of cellulitis in his right leg below a right total knee replacement was started at 7 days post op on IV antibiotics by the service of Infectious Disease. At 11 days post op he presented with persistent cellulitis and was started him on the composition. At 4 weeks post op the cellulitis had resolved.

A 43 year old woman who experienced remote trauma to her right foot that has resulted in chronic edema in her foot develops recurrent episodes of cellulitis once or twice a year. Her typical treatment involved a course of oral antibiotics. She presented with an episode of cellulitis and was treated with a 4 day course of the composition.

A 9 year old girl who experienced a mosquito bite on her right elbow presented 24 hours later with redness, swelling and pain and started on a course of the composition twice per day. Her infection resolved after 3 days of treatment, surprisingly without the use of oral antibiotics.

Pre-Surgical Experimental Results

George

A cream as described above, but wherein Clindamycin was substituted for Cephalexin, was tested on George. The two 25 sq cm areas 20,22 were selected on the right forearm of George, as indicated by FIG. 1. In one 20 of the areas, about 0.5 grm of the cream was applied. Nothing was applied to the other area 22. The same procedure was repeated on the left arm, as indicated by FIG. 2. Cream was applied to area 24; area 26 was untreated. After an hour, a RODAC plate was placed over each area 20,22,24,26 and incubated at 37.5 C for 4 days. After 4 days, colony forming units were counted in each plate as follows: area 20: 25, area 22: 1, area 24: 8, area 26: 5, as shown in FIGS. 3, 4, 5 and 6, respectively. These results clearly suggest that the cream has a residual antibiotic effect.

Silvina

The same cream was tested on Silvina. The two 25 sq cm areas 28,30 were selected on the right forearm of Silvina, as indicated by FIG. 7. In one 28 of the areas, about 0.5 grm of the cream was applied. Nothing was applied to the other area 30. The same procedure was repeated on the left arm, as indicated by FIG. 8. Cream was applied to area 34; area 32 was untreated. After an hour, a RODAC plate was placed over each area 28,30,32,34 and incubated at 37.5 C for 4 days. After 4 days, colony forming units were counted in each plate as follows: area 28: 0, area 30: 4, area 32: 0, area 34: 14, as shown in FIGS. 9, 10, 11 and 12, respectively. These results clearly suggest that the cream has a residual antibiotic effect.

Analysis

Persons of ordinary skill will readily appreciate that the post-surgical embodiment of the invention has significant advantage in that the use of IV and oral antibiotics can be reduced, thereby avoiding the risk of side effects or complication associated with IV treatment and the risk of gastrointestinal side effects and allergic reactions associated with oral antibiotics.

Persons of ordinary skill will also appreciate, having regards to the demonstrated utility of the Cephalexin cream in the treatment of post-surgical cellulitis, and having regards to the experiences of George and Silvina regarding residual antibiotic effect, that it is reasonable to speculate that the pre-surgical embodiment of the invention, i.e. application of the Cephalexin cream prior to surgical intervention, is likely to reduce the instances of cellulitis infection.

Variations

Whereas a specific embodiment is herein described, variations are possible.

For example, whereas a specific composition is mentioned, the active components therein could of course be varied, as could the base.

Further, whereas the post-operative embodiment describes application to the area of the skin affected by cellulitis, it will be appreciated that strict adherence to this is not necessary; not all of the affected skin need receive the composition, and the composition can be applied to unaffected skin, but it is contemplated that if the medication is at least focused towards the affected area, the treatment will be more effective.

Similarly, in the pre-operative embodiment, it is contemplated that the antibiotic can usefully be applied at any time in the twelve hour period preceding the surgery, but there may be advantage if application is completed relatively near in time to the surgery, such as 30 to 90 minutes prior to surgery, such that the antibiotic has fully penetrated the skin yet remains active.

Further, whereas specific uses are mentioned, other uses are contemplated. Without limitation, the composition could be used in at least the following:

postoperative applications upon any signs of wound redness or drainage, or where wound contamination is a risk [ie. hernia or anterior THR (total hip) surgery, vascular surgery around the groin, any surgical incision around the groin or axilla] or after cosmetic procedures of breast and face emergency rooms applications for dog bite, cat bite, human bite, for treatment or prevention of secondary infection after mosquito or tick bites, or after stitching of lacerations internal medicine/infection disease applications such as cellulitis, diabetic foot ulcers or infections, infected olecranon bursitis or patellar bursitis, severe acne or to treat wounds contaminated with Methicillin-resistant Staphylococcus Aureus (MRSA)

Appropriate dosages have not been established for pediatrics, pregnant women or nursing women and the composition should not be used in such applications until suitable dosage has been so established.

The composition should not be used in any of the following: known hypersensitivity to any of the components/excipients; history of hypersensitivity after taking any of the components/excipients, ASA or other NSAIDs; history of asthma, urticaria, angioedema, acute rhinitis or allergic-type reactions after taking any of the components/excipients, ASA or other NSAIDs; where a potential for cross-reactivity between different NSAIDs is likely; history of hypersensitivity or allergy to Cephalexin or other members of the cephalosporin class of antibacterial drugs or to penicillins; history of cutaneous allergy to Ketoprofen, UV blockers or perfumes; history of photosensitivity reactions.

Care should be taken in respect of patients with: active gastric, duodenal or peptic ulcers: active GI bleeding or perforation; regional ulcer; gastritis or ulcerative colitis; cerebrovascular bleeding or other bleeding disorders; inflammatory bowel disease; severe hepatic impairment; active liver disease; severe renal impairment; deteriorating renal disease or renal impairment.

The composition should not be allowed to come into contact with the eyes or mucous membranes and should never be taken by mouth. After application, the hands should be washed, unless they are the site being treated. No gloves needed to apply unless the hand is compromised. Do not occlude. In the event of accidental ingestion, resulting in significant systemic side effects, general therapeutic measures normally adopted to treat poisoning with drugs should be used, which essentially consists of supportive and symptomatic measures The possibility of systemic side effects cannot be completely excluded. Chances of side effects may increase with size and/or duration of dose. The composition should be used with caution by patients under medication for active peptic ulcers in the stomach or duodenum (e.g., proton pump inhibitors or histamine H2 receptor antagonists).

Concomitant use of other products containing any of the components of the composition or non-steroidal anti-inflammatory drugs (NSAIDs) should be monitored. Local irritation, erythema, pruritus or dermatitis may occasionally occur. Skin photosensitivity, desquamation, discoloration and bullous or vesicular eruptions have been reported in isolated cases. Patients should be warned against exposure to sunlight in order to reduce the incidence of photosensitivity.

In the event of accidental contact with sensitive surfaces (eye, mucous membranes), bathe with copious amounts of cool tap water. Diarrhea, bloody diarrhea, and colitis (including pseudomembranous colitis) have been reported with the use of all broad-spectrum antibiotics, including macrolides, penicillins and cephalosporins. If significant diarrhea occurs, the drug should be discontinued. Large bowel endoscopy should be considered to establish a definitive diagnosis in cases of severe diarrhea. Therapy should be discontinued if the application site displays signs of significant skin reaction, including swelling, urticaria or vesiculobullous rash. The composition should be used with caution by patients with fluid retention or heart failure, hypertension, liver and kidney failure, renal failure, peptic ulcer and/or on blood thinners (any anticoagulant or thrombolytic agent). The patient should be carefully observed and monitored under these circumstances. Prolonged use of the composition may result in the overgrowth of non-susceptible organisms. Careful observation of the patient is essential. If super-infection occurs during therapy, appropriate measures should be taken.

Accordingly, the invention should be understood to be limited only by the accompanying claims, purposively construed.

The invention claimed is:

1. A method of pre-surgical prophylaxis of cellulitis comprising:
  applying a composition in a therapeutic amount comprising an antibiotic and a transdermal cream topically to skin of a subject to be incised up to 12 hours prior to a surgical incision; and
  allowing the composition to reduce colony forming bacteria on the skin.

2. The method according to claim 1, wherein, in each application, between about 0.25 gram and about 1 gram of the composition is applied to the skin.

3. The method according to claim 1, wherein the composition is applied about twice daily.

4. The method according to claim 1, wherein the composition has a density of about 1 gram per milliliter.

5. The method according to claim 1, wherein the antibiotic is present at about 5% by weight.

6. The method according to claim 5, wherein the antibiotic is Cephalexin.

7. The method according to claim 1, wherein the composition comprises about 5% analgesic by weight.

8. The method according to claim 7, wherein the analgesic is Ketoprofen.

9. The method according to claim 1, wherein the composition comprises about 5% anaesthetic by weight.

10. The method according to claim 9, wherein the anaesthetic is Lidocaine.

11. The method according to claim 1, wherein the composition comprises about 85% transdermal cream by weight.

12. The method according to claim 1, further comprising additional application of more of the composition so long as the cellulitis persists.

13. The method according to claim 1, wherein the skin is defined by an area which extends about 2 cm beyond the incision.

14. The method according to claim 1, wherein the composition is applied, in an amount, of between about 0.5 and about 1 gram.

* * * * *